United States Patent [19]

Henne et al.

[11] Patent Number: 6,001,908

[45] Date of Patent: Dec. 14, 1999

[54] ORGANO-TIN-CONTAINING COMPLEX STABILIZER FOR SYNTHETIC RESIN COMPOSITIONS

[75] Inventors: Peter Henne, Greiz; Volker Horn, Berg am Elster; Peter Klass, Greiz, all of Germany; Gerard Hubert Frans Schmetz, Horn, Netherlands; Jack James Angus Orchison, Leigh; Malcolm Thomas John Mellor, Bolton, both of United Kingdom

[73] Assignee: Akcros Chemicals, Eccles, United Kingdom

[21] Appl. No.: 09/099,250

[22] Filed: Jun. 18, 1998

Related U.S. Application Data

[63] Continuation of application No. PCT/EP96/05882, Dec. 20, 1996.

[30] Foreign Application Priority Data

Dec. 21, 1995 [EP] European Pat. Off. .............. 95203595

[51] Int. Cl.$^6$ .................. C08K 5/57; C07F 7/22
[52] U.S. Cl. ............................. 524/178; 556/87
[58] Field of Search ................ 524/178; 556/87

[56] References Cited

U.S. PATENT DOCUMENTS

| | | | |
|---|---|---|---|
| 5,106,898 | 4/1992 | Nosu et al. ........................ | 524/436 |
| 5,109,046 | 4/1992 | Larkin et al. ..................... | 524/178 |
| 5,238,605 | 8/1993 | Abeler et al. ..................... | 524/430 |
| 5,352,723 | 10/1994 | Tanno et al. ..................... | 524/436 |

FOREIGN PATENT DOCUMENTS

| | | | |
|---|---|---|---|
| 189899 | 8/1986 | European Pat. Off. .......... | C08K 3/24 |
| 256872 | 2/1988 | European Pat. Off. ........ | C08K 13/02 |

*Primary Examiner*—Veronica P. Hoke
*Attorney, Agent, or Firm*—Richard P. Fennelly

[57] ABSTRACT

The invention relates to a organo-tin-containing complex stabilizer for synthetic resin compositions of the formula I:

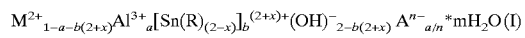

$$M^{2+}_{1-a-b(2+x)}Al^{3+}_a[Sn(R)_{(2-x)}]_b^{(2+x)+}(OH)^-_{2-b(2+x)}A^{n-}_{a/n}*mH_2O\ (I)$$

wherein $M^{2+}$ stands for at least one divalent metal cation, R stands for a $C_{1-12}$ linear or branched alkyl group, $A^{n-}$ stands for an n-valent anion or mixtures of anions, and the following conditions apply:

$$0<a<0.5;\ 0<b<0.1;\ 0\leq x\leq 1;\ 0<a+b(2+x)<0.5;\ 0\leq m\leq 2.$$

The invention also relates to a method for the preparation of these stabilizers and their use in synthetic resin compositions, preferably halogen-containing synthetic resin compositions, or (co)polymers obtained by Ziegler Natta polymerization processes.

17 Claims, No Drawings

ORGANO-TIN-CONTAINING COMPLEX STABILIZER FOR SYNTHETIC RESIN COMPOSITIONS

This is a continuation of PCT Application No. PCT/EP96/05882, filed Dec. 20, 1996.

The invention relates to an organotin-containing complex stabilizer for synthetic resin compositions which comprises an aluminum cation and at least one divalent metal cation, as well as organotin, and which is used for stabilizing synthetic resin compositions, preferably halogen-containing synthetic resin compositions. The invention also relates to a process for the preparation of these stabilizers.

Synthetic resin compositions, especially halogen-containing synthetic resin compositions, are subject to degradation under the influence of heat or light, such as loss of mechanical properties and/or discoloration. Therefore, it is the practice to incorporate compounds with a stabilizing activity into the synthetic resin compositions. Metal-containing stabilizers for this purpose have been known for quite some time. In the early days heavy metals such as cadmium and lead were present, but these are replaced nowadays by calcium, magnesium, and zinc compounds in demanding applications such as pipes, cables, and window profiles. Then layered compounds comprising divalent and trivalent metal cations and, optionally, different anions were found to be a class of compounds with particularly good stabilization properties. In the literature referred to, such stabilizers are frequently found under the name of hydrotalcite.

To improve not only the stabilizing activity, but also the initial color and the avoidance of discoloration phenomena, the above-mentioned hydrotalcites are combined with other stabilizers. A frequently found combination is the one with organotin esters, since such compounds have proved to be excellent thermal stabilizers on the one hand, while on the other they have an extremely good effect on the initial color and the transparency. Preferred organotin esters are alkyl-tin mercaptides, which use results in resins with improved thermostability and initial color when compared to sulfur-free organotin esters. However, these advantageous properties are countered by the drawback of odor problems resulting from the use of the organotin mercaptides. Moreover, the use of organomercaptides influences negatively the rheology and the Vicat softening temperature of the compositions. A combination of hydrotalcite containing two divalent metal cations and one trivalent metal cation with an organotin mercaptide has been described in EP-A-0 189, 899.

Additionally, EP-A-0-256,872 discloses hydrotalcites in combination with magnesium oxide to stabilize synthetic resin compositions. However, these hydrotalcites have to be combined with either organotin stabilizers or with a mixture of beta-diketone and organic acid salts of zinc.

Finally, in certain applications for synthetic resin compositions, such as cables, good electrical properties are additionally required, such as resistance to water absorption.

Accordingly, it is an object of the present invention to provide a stabilizer which, when compared to conventional hydrotalcite stabilizers, improves the thermal stability, improves the initial color, gives no odor, and improves the resistance to water absorption of the resins in which they are incorporated. It is another object to provide a preparation process for such a stabilizer. Finally, it is an object of the present invention to provide synthetic resin compositions comprising the stabilizer of the present invention having the improved properties mentioned above. Surprisingly, it has been found that the stabilizers of the present invention even improve the thermostability of the compositions compared to the combination of hydrotalcite and organotin stabilizers mentioned above.

The present invention comprises a organotin-containing complex stabilizer of the following formula I:

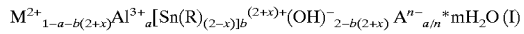

$$M^{2+}{}_{1-a-b(2+x)}Al^{3+}{}_a[Sn(R)_{(2-x)}]_b{}^{(2+x)+}(OH)^{-}{}_{2-b(2+x)} A^{n-}{}_{a/n} * mH_2O \quad (I)$$

wherein $M^{2+}$ stands for at least one divalent metal cation, R stands for a $C_{1-12}$ linear or branched alkyl group, $A^{n-}$ stands for an n-valent anion or mixtures of anions, and the following conditions apply:

$$0<a<0.5;\ 0<b<0.1;\ 0\leq x\leq 1;\ 0<a+b(2+x)<0.5;\ 0\leq m\leq 2.$$

Preferably, the stabilizers of the present invention comprise two divalent cations. Examples of the divalent cation include Mg, Zn, Ca, Ba, Sr, and Sn. Preferably, the R group is selected from the group of methyl, butyl, octyl, and dodecyl groups. Examples of the anions include carbonate, hydrogen carbonate, sulfate, phosphate, nitrate, nitrite, chlorate, hydroxyl, acetate, salicylate, maleate, phthalate, acetylacetonate, and halogen, such as chloride, and mixtures thereof. Preferably, the following conditions apply:

$$0.25<a<0.5;\ 0<b<0.05;\ 0\leq x\leq 1;\ 0.25<a+b(2+x)<0.5;\ 0\leq m\leq 1.$$

Examples of the organotin-containing complex stabilizers are:

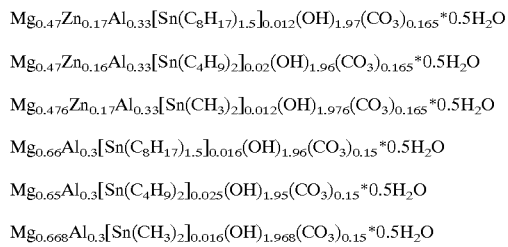

$Mg_{0.47}Zn_{0.17}Al_{0.33}[Sn(C_8H_{17})_{1.5}]_{0.012}(OH)_{1.97}(CO_3)_{0.165}*0.5H_2O$ $Mg_{0.47}Zn_{0.16}Al_{0.33}[Sn(C_4H_9)_2]_{0.02}(OH)_{1.96}(CO_3)_{0.165}*0.5H_2O$ $Mg_{0.476}Zn_{0.17}Al_{0.33}[Sn(CH_3)_2]_{0.012}(OH)_{1.976}(CO_3)_{0.165}*0.5H_2O$ $Mg_{0.66}Al_{0.3}[Sn(C_8H_{17})_{1.5}]_{0.016}(OH)_{1.96}(CO_3)_{0.15}*0.5H_2O$ $Mg_{0.65}Al_{0.3}[Sn(C_4H_9)_2]_{0.025}(OH)_{1.95}(CO_3)_{0.15}*0.5H_2O$ $Mg_{0.668}Al_{0.3}[Sn(CH_3)_2]_{0.016}(OH)_{1.968}(CO_3)_{0.15}*0.5H_2O$

The present invention also comprises a preparation process for the organotin-containing complex stabilizer. Hereto an organotin compound is introduced during the manufacturing process for the stabilizer. This process typically comprises a first step wherein primary particles are formed and a second step during which a more regular crystallization with change in form and size takes place. The organotin compound may be added at any point of the first step in the process. In a preferred process an organic tin salt is combined with at least one divalent metal cation source in an aqueous system at the beginning of said first reaction step, whereafter an aluminum source is added to form the primary particles of the organotin-containing complex stabilizer. The reaction is carried out at elevated temperatures, preferably between 50 and 200° C., more preferably between 60 and 160° C. The desired pH range is between 9 and 12, preferably, between 10 and 12. When a basic aluminum compound is applied, the pH is set automatically. Otherwise, base compounds such as alkali hydroxide, e.g., sodium hydroxide, have to be present.

The divalent metal cation compound is selected from the salts, oxides, hydroxides, and mixtures thereof. Examples include zinc sulfate, zinc oxide, magnesium chloride, magnesium oxide, magnesium carbonate, and basic magnesium carbonate ($4MgCO_3*Mg(OH)_2*4H_2O$). Aluminum is added in the form of reactive hydroxide, oxide or of its salt, e.g., aluminum sulfate or sodium aluminate.

The organotin source is preferably selected from an alkyl tin trichloride or dialkyl tin dichloride or mixtures thereof, e.g., dimethyl tin dichloride, octyl tin chloride (a composition comprising octyl tin trichloride and dioctyl tin dichloride), and dibutyl tin dichloride.

Preferably, a certain time period elapses before the aluminum source is added to the reaction mixture of the divalent metal source(s) and organotin salt. More particularly, the first adduct is aged during a time period ranging from 15 minutes to 5 hours before the aluminum source is added.

The incorporation of the anions is carried out in a simple manner through the use of the corresponding salts of the divalent metals, such as the above-mentioned carbonate, hydrogen carbonate, sulfate, phosphate, nitrate, nitrite, chlorate, hydroxyl, acetate, salicylate, maleate, phthalate, acetylacetonate, and halogen, such as chloride, and mixtures thereof, through the addition of the anions as alkali salt solution, such as the addition of $NaHCO_3$, or by leading carbon dioxide through the suspension.

If the organotin compound is incorporated in the first process step, the thereby obtained complex stabilizer will have a reduced average particle size. Typically, the addition of the organotin compound leads to primary particles with an average particle size of 100–200 nm, compared to about 500 nm when the organotin compound is not used. A correlation of the reduced primary particle size and improved performance of the stabilizer is likely, however, the Applicant does not want to be limited to such theory.

The thus formed organotin-containing stabilizer complex is filtered and washed with water until it is free of salt and optionally subjected to a second process step, which is known in the art as a hydrothermal treatment, optionally under the corresponding vapor pressure. Subsequently, it may also be subjected to a surface treatment known in the art, applying a coating onto the complex.

For the surface treatment, which is a preferred embodiment of the present invention, use may be made of known substances such as fatty acids, salts, and esters thereof, glycerin esters, and silanes. Examples include stearic acid, sodium stearate, zinc stearate, tetraalkoxy silane, and vinyl alkyloxy silane. The amount of coating compound to be added is in the range of 1 to 6 wt %, preferably 2 to 5 wt %, calculated on the prepared organotin-containing complex stabilizer.

Without wishing to be so restricted, applicant believes that the organotin containing complex stabilizer has a layered structure, e.g., a hydrotalcite structure. By reaction with a Grignard reagent and subsequent gas chromatographic analysis, it was demonstrated that the organic groups of the organotin moiety of the stabilizer remained to be covalently bonded to the tin atom.

The so-formed organotin-containing complex stabilizer is used in synthetic resin compositions, such as halogen-containing resin compositions, e.g., polyvinyl chloride, or polyolefin (co)polymers obtained by Ziegler-Natta polymerizations. In these compositions costabilizers may be present as well as lubricants, plasticizers, fillers, and impact strength modifiers. The compositions of the present invention are applied, inter alia, in profiles, sheets, pipes, cables, and household articles.

The invention will be further illustrated by the following Examples.

EXAMPLES

A) Preparation of complex stabilizers containing two divalent metal cations

Example 1

In 1500 ml of deionized water were suspended, with stirring, 14.5 g of $ZnSO_4*7H_2O$, 28.0 g of $MgCl_2*6H_2O$, 13.0 g of NaOH (solid), and 30.0 g of $NaHCO_3$, and the whole was heated to 80° C. After continuous stirring for thirty minutes, 1.30 g of octyl tin chloride (Sn content 31.8%, monooctyl:dioctyl molar ratio 1:1) were added dropwise at 80° C. within two minutes. The suspension was stirred for two hours. Subsequently, 29.0 g of a solution of $Al_2(SO_4)_3*14H_2O$ in 250 ml of deionized water were dosed within ten minutes. After four hours, the product was hot filtered and was washed with 2 l of deionized water to make the product salt-free. Next, the filter cake was suspended in 1 l of deionized water and subjected to a hydrothermal treatment, firstly for two hours at 90° C. and then for five hours at 160° C. at the corresponding vapor pressure. After this the product was cooled down to 90° C. and coated with 1.2 g of sodium stearate. After ten minutes the solid matter was filtered off hot and was dried at 110° C. to constant weight.

After milling, the average particle diameter was 0.99 μm and the specific surface area was 16 m²/g. The yield was 25.3 g.

Analysis of the material yielded the following result:

13.2 of Mg 12.9% of Zn 10.5% of Al 1.6% of Sn

This result was indicative for a complex stabilizer of the formula:

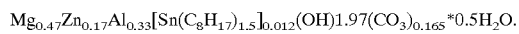

$Mg_{0.47}Zn_{0.17}Al_{0.33}[Sn(C_8H_{17})_{1.5}]_{0.012}(OH)1.97(CO_3)_{0.165}*0.5H_2O$.

Example 2

Into 1500 ml of deionized water were stirred 66.0 g of basic magnesium carbonate, i.e., 4 $MgCO_3*Mg(OH)_2*4H_2O$, and 20.0 g of ZnO, and the whole was heated to 85° C. After thirty minutes, 9.2 g of dibutyl tin dichloride (Sn content 39.06%) were added dropwise at 85° C. within ten minutes. The suspension was stirred for one hour, whereupon at 85° C. 138.0 g of a 29.9% solution of sodium aluminate ($Al_2O_3$ content 18.6%) were added within ten minutes. After four hours, the solid matter was filtered off hot and washed salt-free with 1 l of deionized water. The filter cake was subsequently suspended in 1.5 l of deionized water and subjected to a hydrothermal treatment, firstly at 95° C. for four hours and then for four hours at 140° C. at the corresponding vapor pressure. Next, the product was cooled down to 90° C. and was coated with 3.0 g of stearic acid. The solid matter was filtered off hot and dried at 110° C. to constant weight.

After milling, the average particle diameter was 1.04 μm and the specific surface area was 15 m²/g. The yield was 133.1 g.

Analysis of the material yielded the following result:

12.9% of Mg 12.0% of Zn 10.0% of Al 2.6% of Sn

This result is indicative for a complex stabilizer of the formula:

$$Mg_{0.47}Zn_{0.16}Al_{0.33}[Sn(C_4H_9)_2]_{0.02}(OH)_{1.96}(CO_3)_{0.165}*0.5H_2O.$$

Example 3

Example 1 was repeated, except that 1.30 g of octyl tin chloride was replaced by 0.75 g of dimethyl tin dichloride. After milling, the average particle diameter was 1.02 μm and the specific surface area was 13 m²/g. The yield was 25.3 g.

Analysis of the material yielded the following result:

13.1% of Mg 12.9% of Zn 10.4% of Al 1.6% of Sn

This result is indicative for a complex stabilizer of the formula:

$$Mg_{0.476}Zn_{0.17}Al_{0.33}[Sn(CH_3)_2]_{0.012}(OH)_{1.976}(CO_3)_{0.165}*0.5H_2O.$$

Comparative Example A

In 1500 ml of deionized water were suspended, with stirring, 14.5 g of ZnSO$_4$*7H$_2$O, 31.0 g of MgCl$_2$*6H$_2$O, 12.0 g of NaOH (solid), and 30.0 g of NaHCO$_3$, and the whole was heated to 80° C. The suspension was stirred for two hours. Subsequently, 29.0 g of a solution of Al$_2$(SO$_4$)$_3$*14H$_2$O in 250 ml of deionized water were dosed within ten minutes. After four hours, the product was hot filtered and washed with 2 l of deionized water to make the product salt-free. Next, the filter cake was suspended in 1 l of deionized water and given a hydrothermal treatment, firstly for two hours at 90° C. and then for 5 hours at 160° C. at the corresponding vapor pressure. After this, the product was cooled down to 90° C. and coated with 1.2 g of sodium stearate. After ten minutes the solid matter was filtered off hot and dried at 110° C. to constant weight.

After milling, the average particle diameter was 1.11 μm and the specific surface area was 15 m²/g. The yield was 25.2 g.

Analysis of the material yielded the following result:

14.4% of Mg 13.1% of Zn 10.6% of Al

This result is indicative for a complex stabilizer of the formula:

$$Mg_{0.5}Zn_{0.17}Al_{0.33}(OH)_2(CO_3)_{0.165}*0.5H_2O$$

B) Preparation of complex stabilizers containing one divalent metal cation

Example 4

In 1500 ml of deionized water were suspended, with stirring, 41.8 9 of MgCl$_2$*6H$_2$O, 18.0 g of NaOH (solid), and 27.0 g of NaHCO$_3$, and the whole was heated to 80° C. After continuous stirring for thirty minutes, 1.9 g of octyl tin chloride (Sn content 31.8%, mono-di ratio 1:1) were added dropwise at 80° C. within two minutes. The suspension was stirred for two and one-half hours. Subsequently, 29.0 g of a solution of Al$_2$(SO$_4$)$_3$*14H$_2$O in 250 ml of deionized water were dosed within ten minutes. After four hours, the product was hot filtered and washed with 2 l of deionized water to make the product salt-free. Next, the filter cake was suspended in 1 l of deionized water and given a hydrothermal treatment, firstly for two hours at 90° C. and then for five hours at 160° C. at the corresponding vapor pressure. After this the product was cooled down to 90° C. and coated with 1.2 g of sodium stearate. After ten minutes the solid matter was filtered off hot and dried at 110° C. to constant weight.

After milling, the average particle diameter was 3.41 μm and the specific surface area was 16 m²/g. The yield was 25.4 g.

Analysis of the material yielded the following result:

19.8% of Mg 10.2% of Al 2.4% of Sn

This result is indicative for a complex stabilizer of the formula:

$$Mg_{0.66}Al_{0.3}[Sn(C_8H_{17})_{1.5}]_{0.016}(OH)_{1.96}(CO_3)_{0.15}*0.5H_2O.$$

Example 5

In 1500 ml of deionized water were suspended with stirring 41.3 g of MgCl$_2$*6H$_2$O, 18.0 g of NaOH (solid), and 27.0 g of NaHCO$_3$, and the whole was heated to 80° C. After continuous stirring for thirty minutes, 2.4 g of dibutyl tin dichloride (Sn content 39.06%) were added dropwise at 80° C. within three minutes. The suspension was stirred for one hour. Subsequently, 29.0 g of a solution of Al$_2$(SO$_4$)$_3$*14H$_2$O in 250 ml of deionized water were dosed within ten minutes. The subsequent steps were the same as described in Example 4.

After milling, the average particle diameter was 3.16 μm and the specific surface area was 13 m²/g. The yield was 25.6 g.

Analysis of the material yielded the following result:

19.5% of Mg 10.1% of Al 3.6% of Sn

This result is indicative for a complex stabilizer of the formula:

$$Mg_{0.65}Al_{0.3}[Sn(C_4H_9)_2]_{0.025}(OH)_{1.95}(CO_3)_{0.15}*0.5H_2O.$$

Example 6

In 1500 ml of deionized water were suspended with stirring 44.4 g of $MgCl_2*6H_2O$, 18.0 g of NaOH (solid), and 27.0 g of $NaHCO_3$, and the whole was heated to 80° C. After continuous stirring for thirty minutes 1.15 g of dimethyl tin dichloride (Sn content 54%) were added dropwise at 80° C. within two minutes. The suspension was stirred for one hour. Subsequently, 29.0 g of a solution of $Al_2(SO_4)_3*14H_2O$ in 250 ml of deionized water were dosed within ten minutes. The subsequent steps were the same as described in Example 4.

After milling, the average particle diameter was 3.40 μm and the specific surface area was 15 m²/g. The yield was 25.1 g.

Analysis of the material yielded the following result:

20.5% of Mg 10.5% of Al 2.4% of Sn

This result is indicative for a complex stabilizer of the formula:

$$Mg_{0.668}Al_{0.3}[Sn(CH_3)_2]_{0.016}(OH)_{1.968}(CO_3)_{0.15}*0.5H_2O.$$

Comparative Example B

In 1500 ml of deionized water were suspended with stirring 46.0 g of $MgCl_2*6H_2O$, 17.0 g of NaOH (solid), and 27.0 g of $NaHCO_3$, and the whole was heated to 80° C. The suspension was stirred for two hours. Subsequently, 29.0 g of a solution of $Al_2(SO_4)_3*14H_2O$ in 250 ml of deionized water were dosed within ten minutes. After four hours, the product was hot filtered and washed with 2 l of deionized water to make the product salt-free. Next, the filter cake was suspended in 1 l of deionized water and given a hydrothermal treatment, firstly for two hours at 90° C. and then for five hours at 160° C. at the corresponding vapor pressure. After this, the product was cooled down to 90° C. and coated with 1.2 g of sodium stearate. After ten minutes, the solid matter was filtered off hot and dried at 110° C. to constant weight.

After milling, the average particle diameter was 3.53 μm and the specific surface area was 17 m²/g. The yield was 24.9 g.

Analysis of the material yielded the following result:

22.0% of Mg 10.6% of Al

This result is indicative for a complex stabilizer of the formula:

$$Mg_{0.7}Al_{0.3}(OH)_2(CO_3)_{0.15}*0.5H_2O.$$

C) Performance tests

The organo-tin-containing complex stabilizers according to the invention and the comparative complex stabilizers prepared above were tested for their performance in PVC resin.

Profile Recipe A 100 parts PVC K 68—graft copolymer 1 phr acrylic processing aid 3 phr titanium dioxide 3 phr calcium carbonate 0.2 phr zinc laurate 0.2 phr calcium stearate 0.1 phr stearoyl benzoyl methane 0.3 phr tris(2-hydroxyethyl)isocyanurate 0.2 phr polyethylene wax 0.6 phr distearyl phthalate 0.3 phr bis(2,4-di-t.butylphenyl) pentaerythritol diphosphite phr=parts by weight per hundred parts (by weight) of resin Into this recipe, complex stabilizers as prepared according to Examples 1 to 6 and Comparative Examples A and B were incorporated. When the complex stabilizers of the Comparative Examples were applied, an alkyl tin (2-ethylhexyl) thioglycolate stabilizer (alkyl TTG) was also incorporated into the PVC composition. The alkyl TTG is typically a mixture of dialkyl tin di(2-ethylhexyl) thioglycolate and monoalkyl tin tris(2-ethylhexyl) thioglycolate. Table 1 lists the compositions.

TABLE 1

| Example | Stabilizer | Alkyl TTG |
| --- | --- | --- |
| 1A | 1.2 phr ex. 1 | — |
| 2A | 1.2 phr ex. 2 | — |
| 3A | 1.2 phr ex. 3 | — |
| AA | 1.2 phr comp. ex. A | — |
| AAO | 1.2 phr comp. ex. A | 0.13 phr octyl TTG (15% Sn) |
| AAB | 1.2 phr comp. ex. A | 0.17 phr butyl TTG (18% Sn) |
| AAM | 1.2 phr comp. ex. A | 0.09 phr methyl TTG (21% Sn) |
| 4A | 1.2 phr ex. 4 | — |
| 5A | 1.2 phr ex. 5 | — |
| 6A | 1.2 phr ex. 6 | — |
| BA | 1.2 phr comp. ex. B | — |
| BAO | 1.2 phr comp. ex. B | 0.19 phr octyl TTG (15% Sn) |
| BAB | 1.2 phr comp. ex. B | 0.24 phr butyl TTG (18% Sn) |
| BAM | 1.2 phr comp. ex. B | 0.14 phr methyl TTG (21% Sn) |

Octyl TTG and butyl TTG were supplied by Akcros Chemicals GmbH as Tinstab® OTS 17 MS and Tinstab® BTS 70, respectively. Methyl TTG was supplied by Morton International as Advastab® TM-181-FS.

The compositions were tested for thermostability, odor, and initial color. The thermostability was measured in accordance with the Congo-Red method (DIN 53381 method D) at 190° C. To this end, sheets of 0.4 mm thick were prepared on a two-roll mill at a temperature of 175° C.

The odor of the resin was determined by analyzing the sheets when they were taken from the two-roll mill during the preparation of specimen for the thermostability test.

Measurement of the initial color was carried out with a multispectral measurement technique using the CIE 1976 standard. To this end, 2 mm thick sheets were prepared on the roll mill at 190° C. The diffuse reflectance of the sheets was observed under 10° observer angle by subjecting the sheets to daylight D65 under an angle of 8°. The characteristic of the yellow coloration is the Cielab b*-value.

TABLE 2

| Example | Thermostability (min) | Initial color (b*-value) |
|---|---|---|
| AA | 44.7 | 17.1 |
| AAO | 47.0 | 15.9 |
| 1A | 50.8 | 15.4 |
| AAB | 46.3 | 16.0 |
| 2A | 50.0 | 15.6 |
| AAM | 46.0 | 16.2 |
| 3A | 52.5 | 15.3 |
| BA | 36.2 | 23.2 |
| BAO | 38.9 | 21.1 |
| 4A | 40.0 | 20.3 |
| BAB | 37.0 | 22.9 |
| 5A | 38.6 | 20.9 |
| BAM | 38.1 | 22.0 |
| 6A | 42.7 | 20.0 |

All alkyl-TTG containing samples had a mercaptan-like smell. This smell was absent in the samples comprising a stabilizer according to the invention.

The organotin-containing complex stabilizers of the present invention were also tested in Cable Recipe B, a plasticizer-containing recipe. They were tested for thermostability and water absorption.

Cable Recipe B 100 parts PVCK70

50 phr calcium carbonate 40 phr dioctyl phthalate 0.65 phr zinc laurate 0.2 phr Bisphenol A 0.2 phr natural paraffin Into this recipe, the complex stabilizers prepared according to Examples 1 to 6 or Comparative Examples A and B were incorporated. When the complex stabilizers of Comparative Examples A and B were applied, alkyl TTG was also incorporated into the resin composition. Table 3 lists the resulting compositions.

TABLE 3

| Example | Stabilizer | Alkyl TTG |
|---|---|---|
| 1B | 3.0 phr ex. 1 | — |
| 2B | 3.0 phr ex. 2 | — |
| 3B | 3.0 phr ex. 3 | — |
| AB | 3.0 phr comp. ex. A | — |
| ABO | 3.0 phr comp. ex. A | 0.32 phr octyl TTG (15% Sn) |
| ABB | 3.0 phr comp. ex. A | 0.43 phr butyl TTG (18% Sn) |
| ABM | 3.0 phr comp. ex. A | 0.23 phr methyl TTG (21% Sn) |
| 4B | 3.0 phr ex. 4 | — |
| 5B | 3.0 phr ex. 5 | — |
| 6B | 3.0 phr ex. 6 | — |
| BB | 3.0 phr comp. ex. B | — |
| BBO | 3.0 phr comp. ex. B | 0.48 phr octyl TTG (15% Sn) |
| BBB | 3.0 phr comp. ex. B | 0.60 phr butyl TTG (18% Sn) |
| BBM | 3.0 phr comp. ex. B | 0.34 phr methyl TTG (21% Sn) |

The compositions were tested for thermostability as described above, except for the temperature being changed from 190° to 200° C. Again the alkyl-TTG containing samples smelled bad while the compositions according to the invention did not.

Water absorption for the cable compositions was tested by subjecting 40×40×0.4 mm sheets to deionized water at a temperature of 70° C. for twenty days. The increase in weight in percentage terms was then measured on the dried sheets.

TABLE 4

| Example | Thermostability (min) | Water absorption (%) |
|---|---|---|
| AB | 108.2 | 3.66 |
| ABO | 110.7 | 5.01 |
| 1B | 120.0 | 3.42 |
| ABB | 109.4 | 5.22 |
| 2B | 133.5 | 3.47 |
| ABM | 112.8 | 4.77 |
| 3B | 138.3 | 3.58 |
| BB | 101.9 | 2.11 |
| BBO | 106.1 | 3.01 |
| 4B | 109.0 | 1.95 |
| BBB | 103.3 | 2.60 |
| 5B | 107.6 | 1.73 |
| BBM | 109.4 | 2.55 |
| 6B | 115.2 | 2.03 |

It is clear from Tables 2 and 4 that the organotin-containing complex stabilizers according to the present invention provide improved color resistance, a better smell, and a better resistance to water absorption together with improved thermostability as compared with the stabilizer compositions according to the prior art.

What is claimed is:

1. A organotin-containing complex stabilizer of the following formula I:

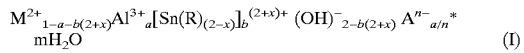

$$M^{2+}_{1-a-b(2+x)}Al^{3+}_a[Sn(R)_{(2-x)}]_b^{(2+x)+}(OH)^-_{2-b(2+x)}A^{n-}_{a/n}*mH_2O \quad (I)$$

wherein $M^{2+}$ stands for at least one divalent metal cation, R stands for a $C_{1-12}$ linear or branched alkyl group, $A^{n-}$ stands for an n-valent anion or mixtures of anions, and the following conditions apply:

$$0<a<0.5;\ 0<b<0.1;\ 0\leq x\leq 1;\ 0<a+b(2+x)<0.5;\ 0\leq m\leq 2.$$

2. A stabilizer according to claim 1 which comprises two divalent cations.

3. A stabilizer according to any one of claims 1–2 wherein the divalent cation is selected from Mg, Zn, Ca, Ba, Sr, and Sn.

4. A stabilizer according to any one claims 1–2 wherein the R group is selected from the group of methyl, butyl, octyl, and dodecyl groups.

5. A stabilizer according to any one of claims 1–2 wherein the anion is selected from the group of carbonate, hydrogen carbonate, sulfate, phosphate, nitrate, nitrite, chlorate, hydroxyl, acetate, salicylate, maleate, phthalate, acetylacetonate, and halogen, such as chloride, and mixtures thereof.

6. A stabilizer according to any one of claims 1–2 wherein the following conditions apply:

$$0.25<a<0.5;\ 0<b<0.05;\ 0\leq x\leq 1;\ 0.25<a+b(2+x)<0.5;\ 0\leq m\leq 1.$$

7. A stabilizer according to claim 6 which is selected from the group consisting of:

$$Mg_{0.47}Zn_{0.17}Al_{0.33}[Sn(C_8H_{17})_{1.5}]_{0.012}(OH)_{1.97}(CO_3)_{0.165}*0.5H_2O$$

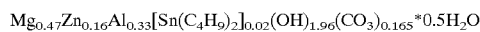

$$Mg_{0.47}Zn_{0.16}Al_{0.33}[Sn(C_4H_9)_2]_{0.02}(OH)_{1.96}(CO_3)_{0.165}*0.5H_2O$$

$$Mg_{0.476}Zn_{0.17}Al_{0.33}[Sn(CH_3)_2]_{0.012}(OH)_{1.976}(CO_3)_{0.165}*0.5H_2O$$

$$Mg_{0.66}Al_{0.3}[Sn(C_8H_{17})_{1.5}]_{0.016}(OH)_{1.96}(CO_3)_{0.15}*0.5H_2O$$

$$Mg_{0.65}Al_{0.3}[Sn(C_4H_9)_2]_{0.025}(OH)_{1.95}(CO_3)_{0.15} * 0.5H_2O$$

$$Mg_{0.668}Al_{0.3}[Sn(CH_3)_2]_{0.016}(OH)_{1.968}(CO_3)_{0.15} * 0.5H_2O.$$

8. A stabilizer according to any one of claims 1–2 which has a coating of 1 to 6 wt % coating compound based on the weight of the stabilizer.

9. A stabilizer according to any one of claims 1–2 which is odor free.

10. A stabilizer according to any one of claims 1–2 wherein the primary particles of the stabilizer have an average particle size of less than 250 nm.

11. An organotin-containing complex stabilizer obtainable by a process comprising a first step in an aqueous system in which at least one divalent metal cation source is reacted with an organotin compound, whereafter an aluminum source is added, the process being carried out at a temperature between 50° and 200° C. and the pH ranges from 9 to 12.

12. A process for the preparation of the organotin-containing complex stabilizer according to any one of claims 1–2 in an aqueous system in a first step at least one divalent metal cation source is reacted with an organo-tin compound, whereafter an aluminum source is added, the process being carried out at a temperature between 50° and 200° C. and the pH ranges from 9 to 12.

13. A process according to claim 12, characterized in that a time period elapses before the aluminum source is added.

14. A process according to claim 12, characterized in that the stabilizer is subsequently subjected to a hydrothermal treatment, optionally under the corresponding vapor pressure.

15. A process according to claim 12, characterized in that the stabilizer is subjected to a surface treatment applying a coating onto the complex.

16. A synthetic resin composition comprising the stabilizer according to any of claims 1–2.

17. An article comprising the synthetic resin according to claim 16.

* * * * *